US009850184B2

(12) United States Patent
Khan et al.

(10) Patent No.: US 9,850,184 B2
(45) Date of Patent: Dec. 26, 2017

(54) TRIPHASIC FLOW MILLIREACTORS

(71) Applicant: National University of Singapore, Singapore (SG)

(72) Inventors: Saif A. Khan, Singapore (SG); Ning Yan, Singapore (SG); Swee Kun Yap, Singapore (SG); Yuan Yuan, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/302,743

(22) PCT Filed: Jun. 19, 2015

(86) PCT No.: PCT/SG2015/050171
§ 371 (c)(1),
(2) Date: Oct. 7, 2016

(87) PCT Pub. No.: WO2015/195051
PCT Pub. Date: Dec. 23, 2015

(65) Prior Publication Data
US 2017/0101358 A1    Apr. 13, 2017

Related U.S. Application Data

(60) Provisional application No. 62/014,742, filed on Jun. 20, 2014.

(51) Int. Cl.
*C07C 5/03* (2006.01)
*B01J 19/00* (2006.01)
*C07C 209/36* (2006.01)

(52) U.S. Cl.
CPC ............. *C07C 5/03* (2013.01); *B01J 19/0093* (2013.01); *C07C 209/36* (2013.01);
(Continued)

(58) Field of Classification Search
CPC .......... B01J 19/0093; B01J 2219/00896; B01J 2219/00903; B01J 2219/00813; B01J 2219/00867; B01J 2219/00862
See application file for complete search history.

(56) References Cited

U.S. PATENT DOCUMENTS 6,759,027 B1    7/2004  Bilardello et al.
2014/0264171 A1*  9/2014  Schut ...................... B22F 9/16
                                                   252/301.4 S

FOREIGN PATENT DOCUMENTS

CN     1962035 A     5/2007
MY     118594 A     12/2004
(Continued)

OTHER PUBLICATIONS

Al-Rawashdeh et al "Design Criteria for a Barrier-Based Gas-Liquid Flow Distributor for Parallel Microchannels" Chemical Engineering Journal vol. 181, pp. 549-556, 2012.
(Continued)

*Primary Examiner* — Lessanework Seifu
(74) *Attorney, Agent, or Firm* — Cesari and McKenna, LLP

(57) ABSTRACT

Disclosed is a reactor system that contains multiple millireactors, each including a millitube, a first feed line, a second feed line, and a third feed line. Each of the first and second feed lines has a hydraulic damper disposed therein. Also disclosed is a process for conducting in a millitube a triphasic flow reaction that requires a liquid reactant, a gas reactant, and a catalyst.

15 Claims, 1 Drawing Sheet

(52) U.S. Cl.
CPC . *C07C 209/365* (2013.01); *B01J 2219/00792* (2013.01); *B01J 2219/00813* (2013.01); *B01J 2219/00835* (2013.01); *B01J 2219/00867* (2013.01); *B01J 2219/00896* (2013.01); *B01J 2219/00903* (2013.01); *C07C 2601/14* (2017.05)

(56) References Cited

FOREIGN PATENT DOCUMENTS

WO WO-2004/091771 A1 10/2004
WO WO2012/152337 A1 * 11/2012

OTHER PUBLICATIONS

Onal et al "Application of a Capillary Microreactor for Selective Hydrogenation of α,β-Unsaturated Aldehydes in Aqueous Multiphase Catalysis" Chemical Engineering & Technology vol. 28, pp. 972-978, 2005.

Yap et al "Triphasic Segmented Flow Millireactors for Rapid Nanoparticle-Catalyzed Gas-Liquid Reactions—Hydrodynamic Studies and Reactor Modeling" Journal of Flow Chemistry vol. 4, pp. 200-205, 2014.

* cited by examiner

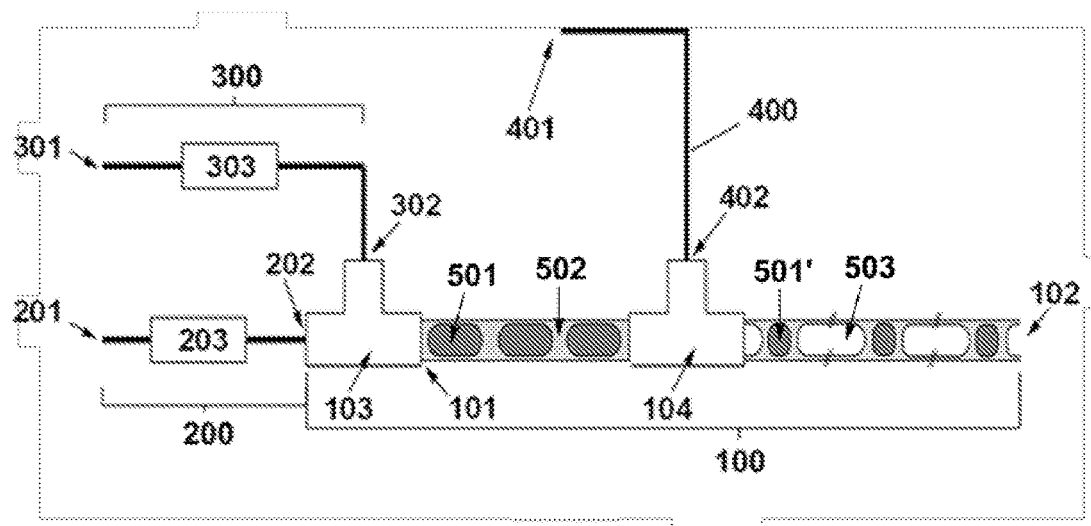

TRIPHASIC FLOW MILLIREACTORS

CROSS REFERENCE TO RELATED APPLICATIONS

This application is the National Stage of International Application No. PCT/SG2015/050171, filed on Jun. 19, 2015, which claims the benefit of US Provisional Application No. 62/014,742, filed on Jun. 20, 2014. The contents of both applications are hereby incorporated by reference in their entirety.

BACKGROUND

Gas-liquid multiphase reactions, such as hydrogenation, carbonylation, and hydroformylation, are commonly used in the syntheses of pharmaceuticals and fine chemicals.

Gas-liquid reactions, typically performed in stirred batch reactors with a gaseous reactant pressurized therein, often encounter mass transport limitations due to small specific interfacial areas. Microreactors have been developed for gas-liquid multiphasic transformations to enhance mass transport.

Yet, there are several drawbacks to current microreactors for gas-liquid reactions. First, catalyst recovery and recycle remains a challenge, especially where the products, unreacted starting materials, and catalyst co-exist in the same liquid phase. Moreover, catalyst deactivation shortens the shelf life of the reactors. Finally, the rate of mass transport is limited for reactions beyond a biphasic setting, e.g., triphasic reactions.

There is a need to develop a new reactor system that does not have the above-mentioned drawbacks.

SUMMARY

The present invention relates to a reactor system containing multiple millireactors, each of which includes a millitube and three feed lines. Unexpectedly, the reactor system exhibits (i) tremendous mass transport acceleration in catalytic organic syntheses and (ii) facile catalyst recovery and recycle.

In one aspect, this invention is a triphasic flow reactor system that contains multiple millireactors.

Each of the millireactors includes a millitube, a first feed line, a second feed line, and a third feed line.

The millitube has a first end, a second end, a first chamber attached to the first end, and a second chamber disposed between the two ends of the millitube. The first feed line has a first end for receiving a first liquid, a second end connected to the first chamber, and a first hydraulic damper disposed between the two ends of the first feed line. The second feed line has a first end for receiving a second liquid, a second end connected to the first chamber, and a second hydraulic damper disposed between the two ends of the second feed line. The third feed line has a first end for receiving a gas and a second end connected to the second chamber. As such, the first chamber is capable of receiving both the first and second liquids, and the second chamber is capable of receiving both the gas and a mixture of the first and second liquids.

The reactor system can further include four containers: a first liquid container, a second liquid container, a gas container, and an outflow container. The first container is connected to a first pump and the first end of the first feed line. The second container is connected to a second pump and the first end of the second feed line. The gas container is connected to the first end of the third feed line. The outflow container is connected to the second end of the millitube. In one example, the first and second pumps are each a peristaltic pump.

The term "millitube" herein refers to a tube that has an inner diameter of 0.5-10 mm, e.g., 1-5 mm Typically, the millitube has a length of 1-50 m, e.g., 2-20 m. It can be made of various materials, such as polytetrafluoro-ethylene, polyether ether ketone, fluorinated ethylene propylene, glass, and metal. During the operation, the tube surface is wetted by an organic phase.

The first and second hydraulic dampers each typically consist of a first tube, a second tube, and a third tube in series. Preferably, the second tube has an inner diameter larger than that of each of the first and third tubes. Also preferably, the first tube has the same length and inner diameter as those of the third tube. In one example, the second tube in the first hydraulic damper is a silicone tube and the second tube in the second hydraulic damper is a viton tube.

In another aspect, this invention is a process for conducting a triphasic flow reaction that requires a liquid reactant, a gas reactant, and a catalyst.

The process includes the following steps: (i) preparing a first liquid containing the catalyst, a second liquid containing the liquid reactant, and a gas containing the gas reactant, the first liquid and the second liquid being immiscible; (ii) mixing the first liquid with the second liquid to form a two-phase mixture; (iii) mixing the gas with the two-phase mixture to form a three-phase mixture; (iv) placing the three-phase mixture in a millitube to form gas bubbles; (v) reacting the liquid reactant, the gas reactant, and the catalyst to form a product; and (vi) collecting the product thus formed.

The catalyst is dispersed or dissolved in a first solvent to form the first liquid. Examples of the first solvent include water, ethanol, and isopropanol. The catalyst can be a regular transitional metal catalyst (e.g., Rh-TPPTS complex, where TPPTS is triphenylphosphine trisulfonate sodium or 3,3',3"-phosphanetriyltris(benzenesulfonic acid) trisodium salt) or a nanoparticle catalyst. Exemplary nanoparticle catalysts each contain rhodium, ruthenium, platinum, palladium, iridium, gold, or a combination thereof.

The second liquid can be formed by dissolving the liquid reactant in a second solvent. Examples of the liquid reactant include an alkene compound, a nitro compound, and an aldehyde. Exemplary second solvents are hydrocarbon solvents, e.g., hexane and heptane.

The gas bubbles, formed in the millitube having an inner diameter of 1-5 mm, each have a length of 30-750 mm Further, the ratio of the length of each gas bubble to the inner diameter of the millitube is 30-150.

The gas can contain a carrier gas, e.g., $N_2$ or Ar, and a gas reactant, e.g., $H_2$, CO, $O_2$, $F_2$, or $Cl_2$.

Generally, the flow rate of the gas far exceeds that of liquid phases (e.g., the first liquid and the second liquid), preferably, the former being 20-100 folds (e.g., 30 folds) higher than the latter.

The details of the invention are set forth in the description below. Other features, objects, and advantages of the invention will be apparent from the following drawing and detailed description of several embodiments, and also from the appending claims.

BRIEF DESCRIPTION OF THE DRAWING

FIG. 1 is a schematic illustration of the millireactor of a reactor system according to one embodiment of the present invention.

DETAILED DESCRIPTION

Within this invention is a reactor system containing multiple millireactors for conducting multiphasic flow reactions.

Referring to FIG. 1, each of the millireactors includes a millitube (100) and three feed lines (200, 300, 400). The millitube, 1 mm to 5 mm in inner diameter and 2 m to 20 m in length, has a first end (101), a second end (102), a first chamber (103) attached to the first end (101), and a second chamber (104) disposed between the two ends thereof. The first feed line (200) has a first end (201) for receiving a first liquid, a second end (202) connected to the first chamber (103), and a first hydraulic damper (203) disposed between the two ends of the first feed line (200). The second feed line (300) has a first end (301) for receiving a second liquid, a second end (302) connected to the first chamber (103), and a second hydraulic damper (303) disposed between the two ends of the second feed line (300). The third feed line (400) has a first end (401) for receiving a gas and a second end (402) connected to the second chamber (104).

The reactor system can further include a first liquid container, a second liquid container, a gas container, an outflow container, a first pump, and a second pump, which are not shown in FIG. 1. The first container for holding a first liquid is connected to the first pump and the first end (201) of the first feed line (200). The second container for holding a second liquid is connected to the second pump and the first end (301) of the second feed line (300). The gas container for holding a gas is connected to the first end (401) of the third feed line (400). The outflow container for receiving a liquid mixture containing products is connected to the second end (102) of the millitube (100).

In a typical reactor system, there are multiple parallel millireactors (e.g., eight) for rapid transitional metal-catalyzed gas-liquid reaction (e.g., hydrogenation) and the first and second pumps are each a peristaltic pump.

The two hydraulic dampers (203, 303) in each millireactor serve to damp out pressure fluctuations or flow rate fluctuations resulting from the peristaltic pumps, thereby allowing for formation of a smooth triphasic flow in all millireactors.

An exemplary hydraulic damper consists of three tubes connected in series, namely, a first tube, a second tube, and a third tube. Preferably, the first tube and the third tube have the same length and same inner diameter, and these two tubes have their length and inner diameter smaller than that of the second tube. For instance, the hydraulic dampers each consist of a first tube of 50 mm in length and 0.1 mm in inner diameter, a second tube of 80 mm in length and 4.8 mm in inner diameter, and a third tube of 50 mm in length and 0.1 mm in inner diameter in series. Each of the three tubes can be a polytetrafluoroethylene tube, a silicone tube, or a viton tube. It is preferred that the second tube is an elastic tube (e.g., a silicone tube or a viton tube).

Also within this invention is a process for conducting a triphasic flow reaction that requires a liquid reactant, a gas reactant, and a catalyst.

Described in detail below is an exemplary process for performing such a flow reaction using a reactor system set forth above.

A first liquid is prepared by dispersing or dissolving a catalyst in a first solvent. The homogeneous solution thus prepared is stored in a first liquid container. A second liquid can be a neat liquid reactant or produced by dissolving a liquid reactant in a second solvent immiscible with the first solvent and stored in a second liquid container. Both the first and second liquids are drawn from the two liquid containers by peristaltic pumps into the first and second feed lines (200, 300) as shown in FIG. 1, respectively. The first and second liquids are mixed in the first chamber (103) to form a two-phase mixture of first liquid spheres (501) and the second liquid (502). See FIG. 1. A gas containing a carrier gas and a gas reactant is transported via the third feed line (400) and mixed with the two-phase mixture in the second chamber (104) to form in the millitube a three-phase mixture, which contains first liquid segments (501'), the second liquid (502), and gas bubbles (503). Also see FIG. 1. The gas bubbles can be elongated by controlling the gas pressure or the gas flow rate, thus enlarging the interacting surface areas between the gas and the second liquid containing the liquid reactant so as to accelerate mass transport of a reaction. The mass transport within the reaction phase is also accelerated by reducing the second liquid (e.g., organic) segments into thin films, with a thickness of the films ranging from 0.01 to 1 mm. The reaction between the liquid reactant and the gas reactant in the presence of the catalyst then takes place to form a product, which is subsequently collected in an outflow container.

The catalyst used in this process is dispersed or dissolved in the first solvent to form a homogeneous solution. Examples of the first solvent include but are not limited to water, methanol, ethanol, isopropanol, tetrahydrofuran, diethyl ether, heptane, isopropyl acetate, isopropyl amine, acetic acid, and N,N-diisopropylethylamine. The second solvent can also be, among others, water, methanol, ethanol, isopropanol, tetrahydrofuran, diethyl ether, heptane, isopropyl acetate, isopropyl amine, acetic acid, or N,N-diisopropylethylamine Importantly, the two solvents are immiscible with each other. The gas can be a pure gas reactant (e.g., $O_2$) or a mixture of a carrier gas (e.g., Ar) and a gas reactant (e.g., $H_2$).

To ensure a stable flow in the reactor system, it is important that the flow rate of the gas far exceeds that of the liquid phases. The ratio of the gas flow rate to each of the liquid flow rates is, preferably, 20-100 and, more preferably, 30-100. The process of this invention can tolerate a gas pressure of 10 kPa to 5000 kPa (e.g., 101-103 kPa) and a reaction temperature of −150° C. to 500° C. (e.g., 25° C.).

In an exemplary process of hydrogenation of 1-hexene, the catalyst is rhodium nanoparticles each having a diameter of about 3 nm. Referring back to FIG. 1, the first liquid, prepared by dispersing the rhodium nanoparticles in water, is introduced via the first feed line (200) at 20 µLmin$^{-1}$ into the first chamber (103). Simultaneously, the second liquid, prepared by dissolving 1-hexene in cyclohexane, is introduced via the second feed line (300) at 10 µLmin$^{-1}$ into the first chamber (103) to mix with the first liquid to form a biphasic liquid mixture (501, 502). The hydrogen gas at near atmospheric pressure, e.g., 101-103 kPa, is introduced via the third feed line (400) at a flow speed of about 29 mm/s into the second chamber (104) to mix with the biphasic liquid mixture to form a triphasic mixture containing gas bubbles (503) at room temperature. Hydrogenation of 1-hexene in the presence of the rhodium nanoparticles subsequently takes place to produce the product hexane. Unexpectedly, the hydrogenation of 1-hexene using a millireactor is about 30 folds faster than that using a batch reactor, demonstrating tremendous mass transport acceleration achieved in a reactor system of this invention.

A quick comparison between the reactor system of this invention and commercial microreactors reveals that for the hydrogenation of a double bond (C=C) the millireactor is able to achieve catalyst activity at least 60% higher than that of similar hydrogenation conducted in fixed bed microreactors. Following an exemplary process of this invention, the activity of platinum nanoparticles (PtNPs), a catalyst, for hydrogenation of nitrobenzene, is 110 min$^{-1}$ (see Example 2 below), which is twice that achieved by PtNPs immobilized on the walls of a conventional microreactor.

The catalyst used in the triphasic flow reactor system of this invention can be continuously recycled. In one example, a platinum nanoparticle catalyst is unexpectedly recovered and recycled almost to the full extent over the course of 5 hours as evidenced by insignificant loss of its substrate conversion rate.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLE 1

A Comparative Study of Hydrogenation of 1-Hexene between a Millireactor and a Batch Reactor Rhodium nanoparticles (RhNPs) were synthesized using an ethanol reduction method reported in Mu et al., *Catal. Lett.*, 2004, 97, 151-154. More specifically, a mixture of 5 mM of RhCl3.xH2O (Alfa Aesar, Rh 38.5-45.5 wt %) and 0.555 g of polyvinylpyrrolidone (Alfa Aesar, MW 40 k) in 30 mL of ethanol and 20 mL of ultrapure water (Milli-Q, 18.2 MΩ cm at 25° C.) was refluxed at 120° C. for 1 hour. All solvents were then vaporized at 60° C. under reduced pressure to afford a black residue before adding thereto 50 mL of ultrapure water to obtain a 5 mM RhNP stock solution. Following the same protocol, platinum nanoparticles (PtNPs) were prepared using 5 mM of $H_2PtCl_6$.xH2O (Sigma; ≥99.9% trace metal basis), with the addition of 840 µL of 1 M NaOH (Fluka, HPCE) prior to refluxing the solution at 135° C. for 30 minutes. A 5 mM PtNP stock solution was then prepared. The respective 5 mM nanoparticle stock solutions were then diluted to various concentrations (e.g., 0.5 mM) prior to use in both batch and flow experiments.

A batch experiment under atmospheric pressure was performed by attaching to a 50 mL round-bottom flask a balloon with hydrogen gas. 5 mL of 1-hexene and 10 mL of the Rh or Pt nanoparticle solution were introduced into the flask, and the reaction took place at room temperature under a well-stirred condition. The organic phase of the reaction was analyzed using gas chromatography (Shimadzu 2010Plus).

In a flow experiment, a hydrophobic polytetrafluoroethylene (PTFE, 1-mm inner diameter) tube was used to prepare a 2-m long millireactor. A liquid-liquid segmented flow was first formed under ambient conditions by infusing into a chamber both an aqueous RhNP catalyst phase at 20 µL/min and an organic phase containing 800 mM of the substrate 1-hexene (Sigma; ≥99%), dissolved in cyclohexane (Sigma; ≥99.9%), at 10 µL/min Hydrogen gas at near atmospheric pressure (101-103 kPa) was introduced into another chamber, mixed therein with the liquid-liquid segmented flow from the first chamber, to form a triphasic flow. High-speed stereomicroscopic imaging (Basler piA640-210 gm) at 100 to 200 frames per second (fps) was used to observe the flow behavior. Samples of the organic phase collected in an outflow container at the end of the 2-m long millireactor were then analyzed using gas chromatography (Shimadzu 2010Plus). The study was conducted at room temperature.

It was found that the hydrogenation of 1-hexene using the millireactor unexpectedly reached an 80% conversion in as short as 1 minute, compared to 30 minutes required by a batch reactor under ambient conditions. The rhodium nanoparticle catalyst used in this reactor system had a catalyst activity of 634 min$^{-1}$, compared to 21 min$^{-1}$ for the same catalyst used in a batch reactor, in which the catalyst activity was calculated based on the moles of the substrate converted per mole of rhodium atoms per minute.

EXAMPLE 2

A Comparative Study of Hydrogenation of Various Substrates between a Millireactor and a Batch Reactor Hydrogenation of various substrates was performed following the protocols described in Example 1 to compare the reaction efficiency using a millireactor, compared with that using a batch reactor.

A variety of substrates and two different nanoparticle catalysts (RhNP and PtNP) were used in this comparative study. See Table 1 below.

TABLE 1

Comparison of hydrogenation of various substrates between the millireactor and the batch reactor[a]

| Substrate | Millireactor | | | Batch reactor | | |
|---|---|---|---|---|---|---|
| | Residence time (min) | Conversion (%) | Activity[b] (min$^{-1}$) | Residence time (min) | Conversion (%) | Activity[b] (min$^{-1}$) |
| 1-Hexene[c] | 0.9 | 82 | 634 | 30 | 80 | 21 |
| Cyclohexene[d] | 1.2 | 30 | 258 | 60 | 14 | 23 |
| Styrene[e] | 4.9 | 71 | 126 | 60 | 61 | 9 |

TABLE 1-continued

Comparison of hydrogenation of various substrates between the millireactor and the batch reactor[a]

| | Millireactor | | | Batch reactor | | |
|---|---|---|---|---|---|---|
| Substrate | Residence time (min) | Conversion (%) | Activity[b] (min$^{-1}$) | Residence time (min) | Conversion (%) | Activity[b] (min$^{-1}$) |
| Styrene[e,f] | — | — | — | 30 | 53 | 16 |
| Nitrobenzene[g] | 0.9 | 98 | 110 | 45 | 97 | 2 |
| 4-Nitrochlorobenzene[h] | 0.5 | 76 | 229 | 60 | 80 | 2 |

[a]Reactions were performed at room temperature and atmospheric pressure using a 0.5 mM aqueous nanoparticle solution, unless otherwise specified; 2 m and 20 m long millireactors were used for the hydrogenation of 1-hexene and styrene, respectively, whereas a 10 m millireactor was used for the hydrogenation of all other substrates;
[b]Activity is calculated based on the moles of substrate converted per mole of Rh atoms per minute;
[c]Cyclohexane, 800 mM 1-hexene, RhNP;
[d]Neat cyclohexene, RhNP;
[e]Cyclohexane, 870 mM styrene, RhNP;
[f]10 barg;
[g]Diethyl ether, 100 mM nitrobenzene, PtNP; and
[h]50 vol % diethyl ether, 50 vol % dichloromethane, 150 mM nitrochlorobenzene, PtNP.

Referring to Table 1, as a consequence of rapid mass transfer rates, in all cases, the millireactor afforded a higher reaction conversion rate within 10-100 folds lower residence times than the batch reactor under the same reaction conditions. The catalyst activity, defined as the moles of the substrate converted per mole of metal atoms per minute, was 10-50 times higher using the millireactor than using the batch reactor. In particular, selective hydrogenation of styrene to ethylbenzene in the millireactor only took about 5 minutes to achieve a 71% conversion rate under near atmospheric conditions, whereas the same reaction took 60 minutes to reach a 61% conversion rate in the batch reactor under an atmospheric pressure and took 30 minutes to achieve a conversion rate of 53% in the batch reactor under an pressure of 10 barg.

In addition, as shown in Table 1, the hydrogenation of 4-nitrochlorobenzene in the millireactor afforded a selectivity of 89% toward 4-chloroaniline and a 76% conversion rate of the substrate in less than one minute, whereas the batch reactor gave only a selectivity of 20% toward the same product with a similar substrate conversion rate in 60 minutes.

EXAMPLE 3

A Comparative Study of Catalyst Activity in Hydrogenation of Double Bond between a Millireactor and a Batch reactor or a Microreactor Hydrogenation of 1-hexene was performed following the protocols described in Example 1 to compare catalyst reactivity in the millireactor with that in a batch reactor or a microreactor.

Various catalysts were used in this comparative study. See Table 2 below. For known catalysts: [1] see Boudart, *Appl. Catal.*, 1989, 46, 131; [2] see Cruz, *Appl. Catal.*, 1989, 46, 131; see Kunzle et al., *Catal. Today*, 2003, 79-80, 503; and [4] see Lee et al., *Organomet.*, 2001, 20, 794.

TABLE 2

Comparison of catalyst activity

| Catalyst | Reaction phase | Substrate | Solvent | Activity (min$^{-1}$) |
|---|---|---|---|---|
| RhNP[a] | Liquid | 1-Hexene | Cyclohexane | 100-650[b]; 1550[c] |
| Rh-γ-Al$_2$O$_3$ [1] | Liquid | Cyclohexene | Cyclohexane | 70-80[d] |
| Bulk Rh [2] | Gas | Cyclohexene | Nil | 1870[d] |
| Pt-γ-Al$_2$O$_3$ [3] | Liquid | Ethyl pyruvate | Acetic acid | 378[e] |
| HRu(CO)Cl(PCy$_3$)(IMes) [4] | Liquid | 1-Hexene | Benzene | 400[f] |

[a]Reaction was conducted in a millireactor;
[b]Residence time in a millireactor was between 1 and 3.1 min;
[c]Residence time in a millireactor was 16 s;
[d]Reaction was conducted in a batch reactor;
[e]Reaction was conducted in a continuous fixed-bed reactor at 28° C. and 145 bar; and
[f]Reaction was conducted in a batch reactor at 100° C. and 4 atm.

Referring to Table 2, in the hydrogenation of dilute cyclohexene catalyzed by a supported Rh catalyst, the activity was in the range of 70-80 min$^{-1}$, an order of magnitude lower than that achieved in the millireactor, i.e., 100-650 min$^{-1}$. An unexpectedly high activity of 1550 min$^{-1}$ was achieved in the millireactor for RhNP catalyzed 1-hexene hydrogenation, which is comparable to reported results for the gas phase hydrogenation of cyclohexene by bulk Rh metal.

In addition, as shown in Table 2, the catalyst activity of the hydrogenation of C=C carried out in the millireactor unexpectedly outperformed that of a supported Pt catalyst in a fixed bed reactor (i.e., 378 min$^{-1}$) and that of reactions catalyzed by a homogeneous ruthenium complex in a batch reactor (i.e., 400 min$^{-1}$)

EXAMPLE 4

A Study of Catalyst Recovery and Recycle Using a Millireactor

A study was performed to evaluate catalyst recovery and recycle using a millireactor as follows.

A PtNP catalyst used in this study was synthesized following the protocol described in Example 1. 2.775 g of polyvinylpyrrolidone was utilized to prepare 50 mL of a 5 mM nanoparticle stock solution.

Hydrogenation of nitrobenzene in the presence of the PtNP catalyst using the millireactor was performed following the protocol described in Example 1. The reaction mixture was subsequently collected at the outflow container. Forming a layer immiscible with the organic phase, the aqueous catalyst phase was recovered simply by decantation. The recovered catalyst was recycled for use in the same reaction under the same conditions.

Unexpectedly, the substrate conversion rate was maintained at 80-100% across as many as 6 catalytic cycles.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. p Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A reactor system comprising multiple millireactors, each of which includes:
   a millitube having a first end, a second end, a first chamber attached to the first end, and a second chamber disposed between the two ends of the millitube;
   a first feed line having a first end for receiving a first liquid, a second end connected in fluid communication to the first chamber, and a first hydraulic damper disposed between the two ends of the first feed line;
   a second feed line having a first end for receiving a second liquid, a second end connected in fluid communication to the first chamber, and a second hydraulic damper disposed between the two ends of the second feed line; and
   a third feed line having a first end for receiving a gas and a second end connected in fluid communication to the second chamber,
   whereby the first chamber is capable of receiving both the first and second liquids, and the second chamber is capable of receiving both the gas and a mixture of the first and second liquids.

2. The reactor system of claim 1, further comprising:
   a first liquid container connected to the first end of the first feed line, the first container connected in fluid communication to a first pump;
   a second liquid container connected to the first end of the second feed line, the second container connected in fluid communication to a second pump;
   a gas container connected to the first end of the third feed line; and
   an outflow container connected to the second end of the millitube.

3. The reactor system of claim 2, wherein the first and second pumps are each a peristaltic pump.

4. The reactor system of claim 1, wherein the millitube is a polytetrafluoroethylene tube.

5. The reactor system of claim 4, wherein the millitube has a length of 2-20 m and an inner diameter of 1-5 mm.

6. The reactor system of claim 4, wherein the first and second hydraulic dampers each consist of a first tube, a second tube, and a third tube in series, the second tube having an inner diameter larger than that of the first tube and that of the third tube.

7. The reactor system of claim 6, wherein the first tube has the same length and inner diameter as those of the third tube.

8. The reactor system of claim 6, wherein the second tube in the first hydraulic damper is a silicone tube and the second tube in the second hydraulic damper is a viton tube.

9. The reactor system of claim 5, wherein the first and second hydraulic dampers each consist of a first tube, a second tube, and a third tube in series, the second tube in each of the hydraulic dampers having an inner diameter larger than that of the first tube and that of the third tube, the first tube in each of the hydraulic dampers having the same length and inner diameter as those of the third tube, the second tube in the first hydraulic damper being a silicone tube, and the second tube in the second hydraulic damper being a viton tube.

10. The reactor system of claim 2, wherein the millitube is a polytetrafluoro-ethylene tube, a polyether ether ketone tube, a fluorinated ethylene propylene tube, a glass tube, or a metal tube.

11. The reactor system of claim 10, wherein the millitube has a length of 2-20 m and an inner diameter of 1-5 mm.

12. The reactor system of claim 10, wherein the first and second hydraulic dampers each consist of a first tube, a second tube, and a third tube in series, the second tube having an inner diameter larger than that of the first tube and that of the third tube.

13. The reactor system of claim 12, wherein the first tube has the same length and inner diameter as those of the third tube.

14. The reactor system of claim 12, wherein the second tube in the first hydraulic damper is a silicone tube and the second tube in the second hydraulic damper is a viton tube.

15. The reactor system of claim 11, wherein the first and second hydraulic dampers each consist of a first tube, a second tube, and a third tube in series, the second tube in each of the hydraulic dampers having an inner diameter larger than that of the first tube and that of the third tube, the first tube in each of the hydraulic dampers having the same length and inner diameter as those of the third tube, the second tube in the first hydraulic damper being a silicone tube, and the second tube in the second hydraulic damper being a viton tube.

* * * * *